United States Patent [19]

Schohe-Loop et al.

[11] Patent Number: 5,756,517

[45] Date of Patent: May 26, 1998

[54] USE OF BISQUINOLINE COMPOUNDS IN THE TREATMENT OF CEREBRAL DISORDERS

[75] Inventors: Rudolf Schohe-Loop, Wuppertal; Peter-Rudolf Seidel, Köln; William Bullock, Wuppertal; Achim Feurer, Odenthal; Georg Terstappen, Düsseldorf; Joachim Schuhmacher, Wuppertal; Franz-Josef van der Staay, Lohmar/Wahlscheid; Bernard Schmidt, Lindlar, all of Germany; Richard J. Fanelli, Madison, Conn.; Jane C. Chisholm, Clinton, Conn.; Richard T. McCarthy, Madison, Conn.

[73] Assignee: Bayer Aktiengesellschaft, Leverkusen, Germany

[21] Appl. No.: 738,124

[22] Filed: Oct. 25, 1996

[51] Int. Cl.[6] .................. C07D 401/02; A61K 31/47
[52] U.S. Cl. .................. 514/314; 546/153; 546/155; 546/159
[58] Field of Search .................. 546/152, 159, 546/153, 155; 514/314

[56] References Cited

U.S. PATENT DOCUMENTS 3,362,875  1/1968  Strauss .................. 514/310
3,974,279  8/1976  Geizler .................. 514/313

*Primary Examiner*—Zinna Northington Davis
*Attorney, Agent, or Firm*—Sprung Kramer Schaefer & Briscoe

[57] ABSTRACT

The present invention relates to the use of bisquinolines of the general formula

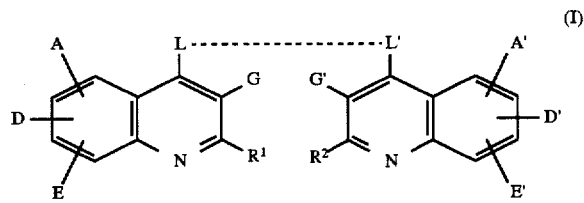

in which the substituents mentioned have the meanings given in the description.

The invention furthermore relates to new bisquinolines of the general formula (I), to a process for the preparation of the known and the new bisquinolines, to the use of the new bisquinolines as medicaments, to their use for the preparation of medicaments, and to medicaments comprising them.

6 Claims, No Drawings

USE OF BISQUINOLINE COMPOUNDS IN THE TREATMENT OF CEREBRAL DISORDERS

The present invention relates to the use of bisquinolines for the preparation and use of medicaments, to novel active ingredients, and to processes for their preparation, in particular to the use as cerebrally active agents.

It has already been disclosed that bisquinolines have an antibacterial, antimalarial and/or antituberculous activity [cf in this context PCT WO 93/07126; PCT WO 95/35287; Chem. Pharm. Bull (1975), 23(8), 1869–73; Arg. Biol. Chem. (1971), 35(1), 119–21].

Moreover, compounds of this type which have an antiparasitic, antimicrobial, antifungal or a hypoglycemic activity and which act as monofunctional AT-selective DNA-intercalating compounds have been published [cf. J. Indian Chem. Soc. (1975), 52(8), 746–9; Ann. Pharm. Fr. (1986), 44(1), 55–64; Pharm. Chem. J. (Engl. Transl.), 26 (1992) 9–10; Khim. Fram. Zh., 266 (1992)) 9,10, 37–39; FEBS Lett. (1988), 228(2), 235–40; Mutat. Res. (1990), 23 (2), 337–43 and Eur. J. Pharmacol. (1986), 1277 (1–2), 27–35].

It has now been found that bisquinolines of the general formula (I)

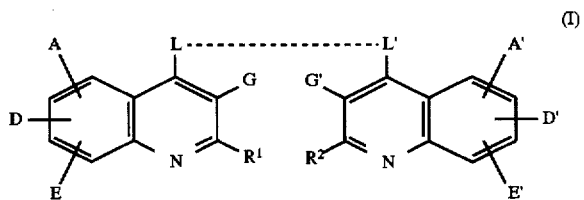

in which

A, A', D, D', E, E', G and G' are identical or different and represent hydrogen, halogen, cycloalkyl having 3 to 8 carbon atoms, aryl having 6 to 10 carbon atoms, cyano, carboxyl, hydroxyl, straight-chains or branched alkyl, alkoxy or alkoxycarbonyl, each of which has up to 8 carbon atoms, or represent a group of the formula —(CO)$_a$—NR$^3$R$^4$
in which
a denotes a number 0 or 1,
R$^3$ and R$^4$ are identical or different and denote hydrogen or straight-chain or branched alkyl having up to 5 carbon atoms, L and L' together represent a radical of the formula

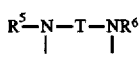

in which
R$^5$ and R$^6$ are identical or different and denote hydrogen, benzyl or straight-chain or branched alkyl having up to 4 carbon atoms
and
T denotes cycloalkyl having 3 to 6 carbon atoms or a straight-chain or branched alkyl chain having up to 10 carbon atoms which is optionally interrupted by an oxygen or sulfur atom, by a group of the formula —SO or —SO$_2$ or by phenyl, pyridyl or cycloalkyl having 3 to 8 carbon atoms and/or which is optionally substituted by phenoxy, spiro-linked cycloalkyl having 3to 8 carbon atoms, hydroxyl or by straight-chain or branched alkoxy having up to 5 carbon atoms, or L and L' together represent a radical of the formula —O—(CH$_2$)$_b$—NR$^7$—
in which
b denotes a number 2, 3, 4, 5, 6 or 7
and
R$^7$ has the abovementioned meaning of R$^5$ and R$^6$ and is identical to or different from this meaning,
and
R$^1$ and R$^2$ represent hydrogen or methyl
and their salts are, surprisingly, ligands of apamine-sensitive potassium channels and thus suitable for use in the control of cerebral diseases.

Physiologically acceptable salts are preferred within the scope of the present invention. Physiologically acceptable salts of the new bisquinolines can be salts of the substances according to the invention with mineral acids, carboxylic acids or sulfonic acids. Particularly preferred are, for example, salts with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

Within the scope of the present invention, the compounds according to the invention may be present in various stereoisomeric forms. The compounds according to the invention exist in stereoisomeric forms which relate to each other either like image and mirror image (enantiomers) or which do not relate to each other like image and mirror image (diastereomers). The invention relates both to the antipodes and to the racemic forms and also the diastereomer mixtures. The racemic forms, like the diastereomers, can be resolved into the stereoisomerically uniform components in a known manner.

Compounds of the general formula (I) which are preferably used in the control of cerebral diseases are those
in which
A, A', D, D', E, E', G and G' are identical or different and represent hydrogen, fluorine, chlorine, bromine, cyclopropyl, cyclobutyl, cyclopentyl, cyclohexyl, phenyl, hydroxyl, straight-chain or branched alky, alkoxy or alkoxycarbonyl, each of which has up to 7 carbon atoms,
or
represent a group of the formula -(CO)a7NR$^3$R$^4$
in which
a denotes a number 0 or 1,
R$^3$ and R$^4$ are identical or different and denote hydrogen or straight-chain or branched alkyl having up to 4 carbon atoms,
L and L' together denote a radical of the formula

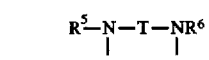

in which
R$^5$ and R$^6$ are identical or different and denote hydrogen, benzyl or straight-chain or branched alkyl having up to 3 carbon atoms
and
T denotes cyclopentyl, cyclohexyl or a straight-chain or branched alkyl chain having up to 8 carbon atoms which is optionally interrupted by an oxygen or sulfur atom, by a group of the formula —SO or —SO$_2$ or by phenyl, pyridyl, cyclopentyl, cyclohexyl or cycloheptyl and/or which is optionally substituted by phenoxy, spiro-linked cyclopentyl or cyclohexyl, hydroxyl or by straight-chain or branched alkoxy having up to 4 carbon atoms, or L and L' together represent a radical of the formula —O—(CH$_2$)$_b$—NR$^7$— in which b denotes a number 2, 3, 4, 5 or 6 and

R$^7$ has the abovementioned meaning of R$^5$ and R$^6$ and is identical to or different from this meaning, and R$^1$ and R$^2$ represent hydrogen or methyl, and their salts.

Compounds of the general formula (I) which are particularly preferably used in the control of cerebral diseases are those in which A, A', D, D', E, E', G and G' are identical or different and represent hydrogen, cyclopropyl, cyclopentyl, cyclobutyl, cyclohexyl, phenyl, fluorine, chlorine, hydroxyl, straight-chain or branched alkyl or alkoxy, each of which has up to 3 carbon atoms, or represent a group of the formula —(CO)$_a$—NR$^3$R$^4$ in which a denotes a number 0 or 1, and R$^3$ and R$^4$ are identical or different and denote hydrogen or straight-chain or branched alkyl having up to 3 carbon atoms, L and L' together represent a radical of the formula

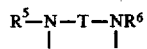

in which

R$^5$ and R$^6$ are identical or different and denote hydrogen, benzyl, methyl or ethyl and T denotes cyclohexyl or a straight-chain or branched alkyl chain having up to 7 carbon atoms which is optionally substituted by an oxygen or sulfur atom, by a group of the formula —SO or —SO$_2$ or by phenyl, pyridyl, cyclopentyl or cyclohexyl and/or which is optionally substituted by phenoxy, spiro-linked cyclohexyl, hydroxyl or by straight-chain or branched alkoxy having up to 3 carbon atoms, or L and L' together represent a radical of the formula —O—(CH$_2$)$_b$—NR$^7$— in which b denotes a number 2, 3, 4 or 5 and

R$^7$ has the abovementioned meaning of R$^5$ and R$^6$ and is identical to or different from this meaning, and R$^1$ and R$^2$ represent hydrogen or methyl, and their salts.

Moreover, the invention relates to new substances whose substituents are defined therein.

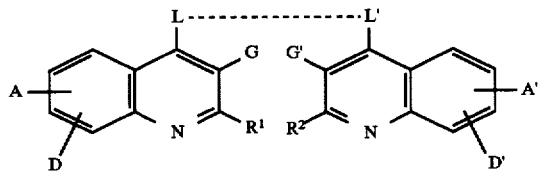

| R$^1$/R$^2$ | A/A' | D/D' | G/G' | L/L' |
|---|---|---|---|---|
| CH$_3$ | H, H | H, H | H, H | |
| H | 7-Cl, 7'-Cl | H, H | H, H | |
| CH$_3$ | H, H | H, H | H, H | |
| CH$_3$ | H, H | H, H | H, H | |
| CH$_3$ | H, H | H, H | H, H | |

-continued

[Structure: Two quinoline rings connected with substituents L, L', G, G', A, A', D, D', R¹, R² as shown]

| R¹/R² | A/A' | D/D' | G/G' | L/L' |
|---|---|---|---|---|
| CH₃ | H, H | H, H | H, H | [structure: -N(H)-CH(CH(OH)CH₃)-(CH₂)₄-N(H)Me  x 2 HCl] |
| CH₃ | H, H | H, H | H, H | [structure: -N(Me)-(CH₂)₆-N(Me)-] |
| CH₃ | H, H | H, H | H, H | [structure: cis-1,2-cyclohexanediamine -N(H)-/-N(H)-] |
| CH₃ | H, H | H, H | H, H | [structure: trans-1,2-cyclohexanediamine -N(H)-/-N(H)-] |
| CH₃ | H, H | H, H | H, H | [structure: 1,3-bis(aminomethyl)benzene -N(H)CH₂-C₆H₄-CH₂N(H)-] |
| CH₃ | H, H | H, H | H, H | [structure: 3,5-bis(aminomethyl)pyridine] |
| CH₃ | H, H | H, H | H, H | [structure: 1,1-disubstituted cyclohexane with -N(H)CH₂- and -(CH₂)₃N(H)-] |
| CH₃ | H, H | H, H | H, H | -HN-CH₂-CH₂-CHCH₃-CH₂CH₂-NH- |
| CH₃ | H, H | H, H | H, H | -HN-CH₂-CH₂-CHOH-CH₂CH₂-NH- |
| CH₃ | H, H | H, H | H, H | -HN-CH₂-CHOH-CH₂-NH- |
| CH₃ | H, H | H, H | H, H | -HN-CH₂-CH(OC₆H₅)-CH₂-NH- |
| CH₃ | H, H | H, H | H, H | -HN-CH₂-CH₂-S-CH₂-CH₂-NH- |
| CH₃ | H, H | H, H | H, H | -HN-CH₂-CH₂-SO-CH₂-CH₂-NH- |
| CH₃ | 5-CH₃, 5'-CH₃ | 7-CH₃, 7'-CH₃ | H, H | -NH-CH₂-CH₂-CH₂-CH₂-CH₂-NH- |
| CH₃ | 6-N(CH₃)₂, 6'-N(CH₃)₂ | H, H | H, H | -NH-CH₂-CH₂-CH₂-CH₂-CH₂-NH- |
| CH₃ | 6-CH(CH₃)₂, 6'-CH(CH₃)₂ | H, H | H, H | -NH-CH₂-CH₂-CH₂-CH₂-CH₂-NH- |
| CH₃ | 5-Cl, 5'-Cl | 8-CH₃, 8'-CH₃ | H, H | -NH-CH₂-CH₂-CH₂-CH₂-CH₂-NH- |
| CH₃ | 6-OCH₃, 6'-OCH₃ | H, H | H, H | -NH-CH₂-CH₂-CH₂-CH₂-CH₂-NH- |
| CH₃ | 8-F, 8'-F | H, H | H, H | -NH-CH₂-CH₂-CH₂-CH₂-CH₂-NH- |
| CH₃ | 7-N(CH₃)₂, 7'-N(CH₃)₂ | H, H | H, H | -NH-CH₂-CH₂-CH₂-CH₂-CH₂-NH- |
| CH₃ | 8-Cl, 8'-Cl | H, H | H, H | -NH-CH₂-CH₂-CH₂-CH₂-CH₂-NH- |
| CH₃ | 6-OCH₃, 6'-OCH₃ | H, H | H, H | [structure: trans-1,3-bis(methylamino-methyl)cyclohexane] |

-continued

| R¹/R² | A/A' | D/D' | G/G' | L/L' | |
|---|---|---|---|---|---|
| CH₃ | 6-OCH₃, 6'-OCH₃ | H, H | H, H | 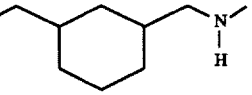 | cis |
| H | 7-CH₃, 7'-CH₃ | 8-CH₃, 8'-CH₃ | CH₃ | 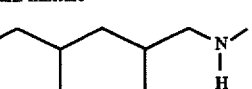 cis/trans mixture | |
| CH₃ | 8-CH₃, 8'-CH₃ | H, H | H, H | 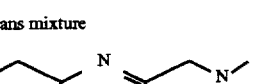 cis/trans mixture | |
| CH₃ | H, H | H, H | H, H | 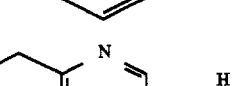 | |
| CH₃ | H, H | H, H | H, H | 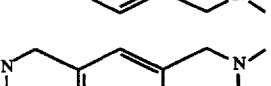 | |
| CH₃ | H, H | H, H | H, H |  | |
| CH₃ | H, H | H, H | H, H | 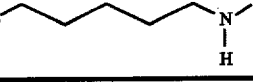 | |
| CH₃ | H, H | H, H | H, H | 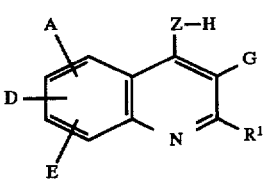 | |

Moreover, there have been found processes for the preparation of the compounds of the general formula ( according to the invention and for the new substances, wherein
[A] 2 equivalents of the compounds of the general formula (II)

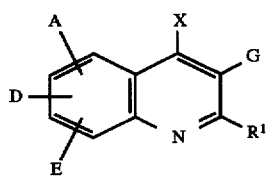 (II)

in which
A, D, E, G and R¹ have the abovementioned meanings and
X represents halogen, preferably fluorine or chlorine, are reacted with compounds of the general formula (III)

HL-L'H (III)

in which
L and L' have the abovementioned meanings,
if appropriate in inert solvents and if appropriate in the presence of a base,
or
[B] 1 equivalent of the compound of the general formula (II) is reacted, in an excess, with the compounds of the general formula (III) under the conditions of process [A] to give compounds of the general formula (IV)

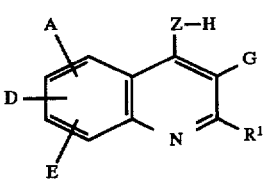 (IV)

in which
A, D, E, G and R have the abovementioned meanings and

Z represents a radical of the formula

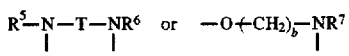

where $R^5$, $R^6$, $R^7$, b and T have the abovementioned meanings and these compounds are then reacted with compounds of the general. formula (IIa)

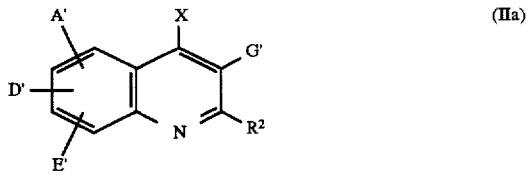

in which

A', D', E', G' and $R^2$ have the abovementioned meanings and

X represents halogen, preferably chlorine, if appropriate in the presence of a base.

The process according to the invention can be exemplified by the following equation:

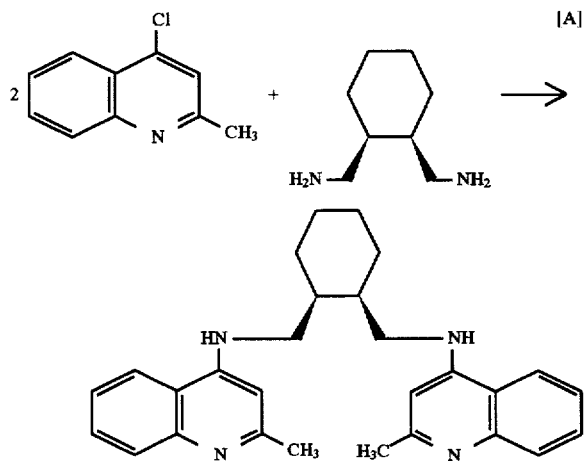

Suitable solvents are the conventional solvents which are not affected by the reaction conditions. These preferably include alcohols such as methanol, ethanol, propanol, isopropanol, hexanol, octanol or phenol, or ethers such as diethyl ether, dioxane, tetrahydrofuran, glycol dimethyl ether or butyl methyl ether, or ketones such as acetone or butanone, or amides such as N-methylpyrrolidone, dim ethylformamide or N -methylphosphorotriamide, or dimethyl sulfoxide, acetonitrile, butyronitrile, ethyl acetate, or halogenated hydrocarbons such as methylene chloride, chloroform or carbon tetrachloride, or pyridine, picoline or N-methylpiperidine. It is also possible to use mixtures of said solvents. Butyronitrile, phenol and N-methylpyrrolidone are preferred. The reaction can also be carried out without a solvent.

Suitable bases are the conventional inorganic or organic bases. These preferably include alkali metal carbonates such as sodium or potassium carbonate, or organic amines such as diethylamine, triethylamine, tripropylamine, pyridine, picoline or N-methylpiperidine, lutidine or diisopropylethylamine. Diisopropylethylamine and tripropylamine are preferred.

Bases which are used for the reaction of the compounds of the general formula (IV) with compounds of the general formula (IIa) are, in accordance with process [B], lithium alkyls, such as n-butyllithium or phenyllithium, alkali metal hydrides such as sodium hydride or potassium hydride, or alkali metal alcoholates such as potassium tert-butanolate. Sodium hydride is preferred.

Suitable iodine salts are alkali metal iodides such as lithium iodide, sodium iodide, potassium iodide and cesium iodide, and tetraalkylammonium iodides such as benzyltributylammonium iodide. It is preferable to use sodium iodide and potassium iodide.

The iodine salts are generally used in an amount of 0.001 to 1 mol, in each case based on 1 mol of the compounds of the general formulae (II)/(IV).

The base is used here in an amount of 0.8 to 5 mol, preferably of 0.8 to 2 mol, in each case based on 1 mol of the compounds of the general formulae (II)/ (IV).

The reactions are generally carried out in the temperature range from -20° C. to the reflux temperature of the solvent, preferably from +20° C. to the reflux temperature of the solvent.

The reaction can be carried out at normal, elevated or reduced pressure (e.g. 0.5 to 5 bar). It is generally carried out at normal pressure.

Some of the compounds of the general formulae (II) and (IIa) are known or they can be prepared by known methods, for example by reacting 2-trifluoromethylaniline with ketones [cf J. Org. Chem. 59, 1994, 5886].

The compounds of the general formula (III) are known per se or can be prepared by conventional methods.

The compounds of the general formula (IV) are known per se or can be prepared by conventional methods.

The compounds according to the invention possess a valuable pharmacological spectrum of action which could not be anticipated.

The compounds according to the invention are ligands for apamin-sensitive potassium channels. This can be shown by studying the affinity to apamin binding sites, e.g. in calves' cerebral membranes. The compounds according to the invention inhibit the ion flux through these channels, as can be shown by rubidium efflux experiments and with electrophysiological methods.

The compounds have a positive influence on learning and memory faculties, as demonstrated by their performance-enhancing action in typical learning and memory models like the water maze, the Morris maze, passive avoidance or reminiscence tests in automated Skinner boxes. They possess an antidepressant potential, as verified by their activity in the Porsolt rat swimming test.

The compounds according to the invention are also suitable for the treatment of myotonic dystrophy, alcoholism and other addiction diseases, of sleep disturbances and of bronchial asthma.

By virtue of their pharmacological properties, the compounds according to the invention can be used for the preparation of drugs for the treatment of degenerative diseases of the central nervous system, e.g. those occurring in cases of dementia (multi-infarct dementia, MD, primary degenerative dementia, PDD, presenile Alzheimer's disease, HIV dementia and other forms of dementia).

They are also suitable for the treatment of age-related cerebral faculty impairment, organic brain syndrome (OBS) and age-associated memory impairment (AAMI).

They are suitable for the treatment of depression and of mania.

1) Binding of $^{125}$I-apamin to calves' cerebral membrane

Calf brains were obtained from the local abattoir. The hippocampus was prepared on ice and a membrane suspension was made up by homogenization twice in buffer (100 mM Tris-HCl, KCl 5 mM, pH 7.4) and centrifugation at 43,000×g. In a total volume of 500 µl, the incubation mixture contained 200 µg of membrane protein, 30 pM $^{125}$I-apamin and test substances in the concentration range $1\times10^{-9}$ to $1\times10^{-4}$M. The non-specific binding of $^{125}$I-apamin was determined in the presence of $1\times10^{-7}$M unlabeled apamin.

After preincubation for 30 min at room temperature (test substances and membrane homogenate), the samples were placed on ice for 10 min before the radioligand was added. The main incubation time was 60 min on ice. When the reaction time had elapsed, an excess of ice-cooled incubation buffer was added to each sample and the mixture was filtered with suction through cellulose acetate/nitrate membrane filters. The amount of bound $^{125}$I-apamin was measured with a gamma counter.

TABLE A

| Ex. no. | $K_i$ (nmol/l) |
| --- | --- |
| 14 | 190 |

Thus, the compounds showed an unexpectedly high affinity to apamin receptors in calf brains.

2) Non-radioactive Rb$^+$ efflux assay for the identification of potassium channel modulators The cellular potassium in PC12 cells is exchanged with rubidium, which is not present in the cells. This exchange is performed by incubating the cells over a period of 4 h in a physiological buffer containing 5.4 mM RbCl without KCl. This rubidium subsequently serves as a tracer for potassium. The cells laden with Rb$^+$ in this way are washed three times and then stimulated by depolarization with 50 mM KCl to open potassium channels (10 min), causing Rb$^+$ to flow out of the cells into the supernatant according to the concentration gradient.

The rubidium contents in the cell supernatant and in the residual cells after they have been lyzed with 1% Triton X-100 are then, determined by means of atomic absorption spectroscopy. The relative proportion of rubidium in the cell supernatant (=Rb$^+$ efflux) is used as a measure of the potassium channel activity.

The effect of substances on the channel activity is measured by co-incubating the test substance over the ten-minute stimulation period and determining its effect on the Rb$^+$ efflux in the manner described above.

TABLE B

| Compound | % inhibition of the Rb efflux at a test concentration of 10 µM |
| --- | --- |
| 15 | 73 |

Thus, the compounds according to the invention show an unexpectedly high inhibitory activity on the apamine-sensitive rubidium efflux in PC 12. cells.

3) Moms maze

Subjects

Male ICR mice, 6–8 wks old and approx 22–28 g, were obtained from Harlan Sprague-Dawley, Inc. (Indianapolis, Ind.) and housed 8/cage with ad libitum access to food and water.

Water Maze Apparatus

The behavioral apparatus consisted of a circular galvanized steel tank painted white with a diameter of 76 cm and divided into four equally spaced quadrants, each containing a plastic fitting that allowed for the placement of an escape platform. Prior to the start of the behavioral testing, the maze was filled daily to a depth of 1 cm above the escape platform (25 cm deep), maintained at a temperature of approx. 22° C., and was made opaque by the addition of 0.9 kg of powdered milk. Numerous stationary visual cues were present in the testing room. The data were recorded with the Multiple Zone Distance Traveled program of the video-V analysis system (Columbus Instruments International Corp., Columbus, Ohio).

Modified Mouse Morris Water Maze Protocol

After a 1 week acclimatization to the animal facility, the mice were given a 90 sec free swim, during which no escape platform was present. One to three days later, acquisition training began and consisted of 4 trials on each day for a total of three days (12 total trials), during which no drugs were given. The mice were randomly assigned a goal quadrant in which the escape platform was located. Animals were then placed in the maze (facing away from the center) at one of four equally spaced positions around the perimeter of the maze. The starting position varied for each mouse until they had started from each of the four positions once daily. On each of the training trials, the mice were allowed 120 sec to find the goal platform. If they failed to do so within the allotted time, they were placed on the platform. The intertrial interval was 30 sec, during which time the mouse remained on the platform. On the fourth day, the mice were given a single 30 sec probe trial in which no escape platform was present. Thirty min or 1 hr prior to the start of the probe trial, mice were randomly assigned to groups that were given either drug or vehicle, and the time spent in each quadrant was measured.

The present invention also includes pharmaceutical formulations which comprise one or more compounds of the general formula (I) together with inert, non-toxic, pharmaceutically appropriate adjuncts and excipients, or which are composed of one or more active substances of the formula (I), and processes for the preparation of these formulations.

The active substances of the formula (I) should be present in these formulations in a concentration of 0.1 to 99.5% by weight, preferably of 0.5 to 95% by weight of the total mixture.

In addition to the active substances of the formula (I), the pharmaceutical formulations can also comprise other pharmaceutical active substances.

The pharmaceutical formulations listed above can be prepared in a conventional manner by known methods, for example with one or more adjuncts or excipients.

To achieve the desired result, it has generally proved advantageous to administer the active substance or substances of the formula (I) in total amounts of about 0.01 to about 100 mg/kg, preferably in total amounts of about 0.01 mg/kg to 10 mg/kg of body weight per 24 hours, optionally in the form of several single doses.

However, it may be advantageous to deviate from said amounts, depending on the nature and body weight of the subject treated, the individual response to the drug, the nature and severity of the disease, the type of formulation and administration and the time or interval at which the drug is administered.

STARTING COMPOUNDS

EXAMPLE I
2,6-Bis-(aminomethyl)-pyridine

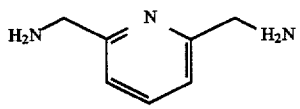

A mixture of 2,6-bis-(hydroxymethyl)-pyridine (556 mg, 4.0 mmol) and triphenylphosphine (1.05 g, 8.0 mmol) was dissolved in THF (20 ml) and cooled to 0° C. Phthalimide (1.2 g, 8.0 mmol) was added, and diethyl azodicarboxylate ester (1.2 ml, 8.0 mmol) was subsequently added dropwise. The cooling bath was removed and the mixture was stirred overnight at RT. The solvent was evaporated on a rotary evaporator, and the residue was purified by chromatography using silica gel (eluent: methylene chloride/ethanol, 100/2). This gives 2,6-bis-(phthalimidomethyl)-pyridine as a solid. m.p.>250° C.

Yield: 1.11 g (70%)

Hydrazine hydrate (2.4 ml, 50 mmol) was added to a solution of 2,6-bis(phthalimidomethyl)-pyridine (1.99 g, 5.0 mmol) and 95% strength ethanol (50 ml). The mixture was refluxed for 3 hours. After cooling, the solvent was evaporated on a rotary evaporator and the residue was purified by chromatography on silica gel (eluent: methylene chloride/ethanol, 100/2). This gives 2,6-bis-(aminomethyl)-pyridine as a yellow oil.

Yield: 690 mg (100%).

NMR (200 MHz, $d_6$-DMSO): $\delta$=7.68 (t, 1H; J=9 Hz); 7.26 (d, 2H, J=9.0 Hz) and 3.78 (s, 4H).

EXAMPLE II
4-Hydroxy-2,5,7-trimethylquinoline

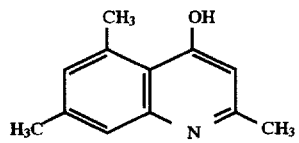

A spatula-tip of p-toluenesulfonic acid was added at room temperature to a solution of 18.15 g (150 mmol) of 3,5-dimethylaniline and 21.45 g (165 mmol) of ethyl acetatoacetate in 150 ml of dichloromethane, and the mixture was refluxed for 16 hours on a water separator. The reaction solution was subsequently concentrated on a rotary evaporator. The residue was taken up in 50 ml of diphenyl ether and added dropwise to 100 ml of boiling diphenyl ether in such a way that the internal temperature always remained >245° C. (metal bath: 280° C.). During this process, an ethanol/diphenyl ether mixture distilled over slowly. After the dropwise addition had ended, stirring was continued for 1 hour at 245°–250° C. The mixture, cooled to room temperature, was treated with 300 ml of n-pentane and stirred overnight. The precipitate was filtered off with suction and washed repeatedly using n-pentane, and the resulting pale beige powder was dried at room temperature under a high vacuum.

Yield: 27.8 g (99%)

m.p.: >240° C.

MS: 187 (100, M$^+$), 158 (22), 144 (19)

EXAMPLE III
4-Chloro-2,5,7-trimethylquinoline

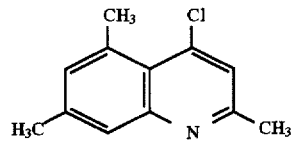

14.0 g (74.9 mmol) of 4-hydroxy-2,5,7-trimethylquinoline (Example II) were slowly introduced into 70 ml of phosphoryl chloride at room temperature. After the mixture had been refluxed for 1 hour, it was cooled to room temperature and then slowly poured into 300 g of ice/water. The temperature was held at 0°–10° C. by means of external cooling. The cooled mixture (internal temperature <150° C.) was subsequently slowly rendered alkaline (>pH 11) using concentrated sodium hydroxide solution. The mixture was extracted three times using in each case 80 ml of dichloromethane. The combined organic phases were washed three times using in each case 100 ml of water, dried over magnesium sulfate and evaporated to dryness on a rotary evaporator, a pale brown solid being obtained as residue.

Yield: 15.0 g (91%)

MS: 205 (100, M$^+$, Cl), 190 (32), 85 (20)

m.p.: 67°–69° C.

General Protocol for Synthesizing the Bis-(Quinolyl)-Diamine (Method A)

The corresponding 4-chloroquinoline derivative (20 mmol) and the diamine (20 mmol) were heated for 16 h at 160° C. under an argon atmosphere. The mixture, cooled to room temperature, was treated with 50 ml of 1N sodium hydroxide solution and 100 ml of dichloromethane and stirred until two homogeneous phases had formed. The organic phase was washed with water until neutral, dried over magnesium sulfate and evaporated to dryness. The product was separated from the residue by column chromatography on aluminum oxide (manufacturer: ICN, Type N Act. I) using dichloromethane/methanol/triethylamine 80/2/1 as the eluent (unless otherwise specified in the tables). The product fractions, which had been evaporated to dryness, were taken up in 80 ml of dichloromethane and washed using 1N sodium hydroxide solution (twice, in each case 30 ml) and water (twice, in each case 30 ml). Drying the organic phase over magnesium sulfate and evaporating it to dryness resulted in the desired product. In some cases, further purification by means of extraction by stirring in a suitable solvent was required (see the notes in the tables).

Yields: 4–50%

(Method B)

10.0 mmol of 4-chloroquinaldine, 4.5 mmol of diamine, 3.3 mmol of phenol and 20 mg of NaI were stirred for 1 hour at 140° under argon. After cooling, the product mixture was separated by flash chromatography on silica gel K60 using dichloromethane/ethanol/ammonia 100:10:1. The crude products thus obtained are either purified by recrystallization or converted into the HCl salts using ethereal hydrochloric acid; the HCl salts are recrystallized from the solvents indicated.

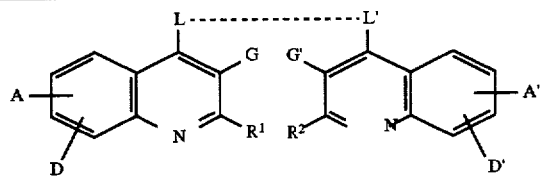

| Ex. No. | $R^1/R^2$ | A/A' | D/D' | G/G' | L/L' | M.p. (°C.)/ $R_f$ value* |
|---|---|---|---|---|---|---|
| 1 | $CH_3$ | H, H | H, H | H, H | —NH—CH₂CH₂—CH(Et)—NH— | 105 |
| 2 | H | 7-Cl, 7'-Cl | H, H | H, H | —NH—CH₂CH₂—CH(Et)—NH— | 140 |
| 3 | $CH_3$ | H, H | H, H | H, H | —NH—CH₂—C(CH₃)₂—CH₂—NH— | 175 |
| 4 | $CH_3$ | H, H | H, H | H, H | —N(Me)—CH₂CH₂CH₂—N(Me)— | $R_f$ = 0.70 (Al₂O₃, CH₂Cl₂/ MeOH/ triethylamine = 80:20:1) |
| 5 | $CH_3$ | H, H | H, H | H, H | —NH—CH₂CH₂—O—CH₂CH₂—NH— | 178 |
| 6 | $CH_3$ | H, H | H, H | H, H | —NH—CH(CH(OH)CH₃)—(CH₂)₃—NH— x 2 HCl | 172 |
| 7 | $CH_3$ | H, H | H, H | H, H | —N(Me)—(CH₂)₆—N(Me)— | $R_f$ = 0,72 |
| 8 | $CH_3$ | H, H | H, H | H, H | cis-1,2-cyclohexanediamine-diyl (—NH—/—NH—) | 105 |
| 9 | $CH_3$ | H, H | H, H | H, H | trans-1,2-cyclohexanediamine-diyl (—NH—/—NH—) | >250 |
| 10 | $CH_3$ | H, H | H, H | H, H | —NH—CH₂—(1,3-C₆H₄)—CH₂—NH— | >250 |

-continued

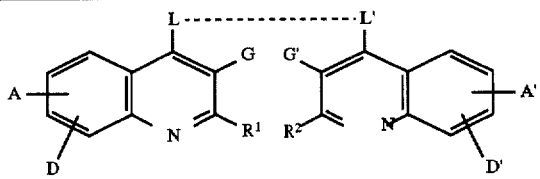

| Ex. No. | $R^1/R^2$ | A/A' | D/D' | G/G' | L/L' | M.p. (°C.)/ $R_f$ value* |
|---|---|---|---|---|---|---|
| 11 | $CH_3$ | H, H | H, H | H, H | ![pyridine-3,5-diyl-bis(methylamine)] | 255 |
| 12 | $CH_3$ | H, H | H, H | H, H | ![1-(aminomethyl)-1-(3-aminopropyl)cyclohexane] | >220 |
| 13 | $CH_3$ | H, H | H, H | H, H | $-HN-CH_2-CH_2-CHCH_3-CH_2CH_2-NH-$ | >300 (x 2 HCl) |
| 14 | $CH_3$ | H, H | H, H | H, H | $-HN-CH_2-CH_2-CHOH-CH_2CH_2-NH-$ | approx. 290 (x 2 HCl) |
| 15 | $CH_3$ | H, H | H, H | H, H | $-HN-CH_2CHOH-CH_2-NH-$ | 210 |
| 16 | $CH_3$ | H, H | H, H | H, H | $-HN-CH_2-CH(OC_6H_5)-CH_2-NH-$ | 134 |
| 17 | $CH_3$ | H, H | H, H | H, H | $-HN-CH_2-CH_2-S-CH_2-CH_2-NH-$ | 184 |
| 18 | $CH_3$ | H, H | H, H | H, H | $-HN-CH_2-CH_2-SO-CH_2-CH_2-NH-$ | 160 |
| 19 | $CH_3$ | 5-$CH_3$, 5'-$CH_3$ | 7-$CH_3$, 7'-$CH_3$ | H, H | $-NH-CH_2-CH_2-CH_2-CH_2-CH_2-NH$ | 159–161° C. |
| 20 | $CH_3$ | 6-$N(CH_3)_2$, 6'-$N(CH_3)_2$ | H, H | H, H | $-NH-CH_2-CH_2-CH_2-CH_2-CH_2-NH$ | 235° C. |
| 21 | $CH_3$ | 6-$CH(CH_3)_2$, 6'-$CH(CH_3)_2$ | H, H | H, H | $-NH-CH_2-CH_2-CH_2-CH_2-CH_2-NH$ | 162° C. |
| 22 | $CH_3$ | 5-Cl, 5'-Cl | 8-$CH_3$, 8'-$CH_3$ | H, H | $-NH-CH_2-CH_2-CH_2-CH_2-CH_2-NH$ | 155° C. |
| 23 | $CH_3$ | 6-$OCH_3$, 6'-$OCH_3$ | H, H | H, H | $-NH-CH_2-CH_2-CH_2-CH_2-CH_2-NH$ | $R_f = 0.25$ a) |
| 24 | $CH_3$ | 8-F, 8'-F | H, H | H, H | $-NH-CH_2-CH_2-CH_2-CH_2-CH_2-NH$ | $R_f = 0.69$ b) |
| 25 | $CH_3$ | 7-$N(CH_3)_2$, 7'-$N(CH_3)_2$ | H, H | H, H | $-NH-CH_2-CH_2-CH_2-CH_2-CH_2-NH$ | 188° C. |
| 26 | $CH_3$ | 8-Cl, 8'-Cl | H, H | H, H | $-NH-CH_2-Ch_2-CH_2-CH_2-CH_2-NH$ | 121–125° C. |
| 27 | $CH_3$ | 6-$OCH_3$, 6'-$OCH_3$ | H, H | H, H | trans-1,3-bis(aminomethyl)cyclohexane | 198° C. |
| 28 | $CH_3$ | 6-$OCH_3$, 6'-$OCH_3$ | H, H | H, H | cis-1,3-bis(aminomethyl)cyclohexane | 239° C. |
| 29 | H | 7-$CH_3$, 7'-$CH_3$ | 8-$CH_3$, 8'-$CH_3$ | $CH_3$ | 1,3-bis(aminomethyl)cyclohexane, cis/trans mixture | 142° C. |
| 30 | $CH_3$ | 8-$CH_3$, 8'-$CH_3$ | H, H | H, H | 1,3-bis(aminomethyl)cyclohexane, cis/trans mixture | 146° C. |
| 31 | $CH_3$ | H, H | H, H | H, H | pyridine-2,6-diyl-bis(methylamine), cis/trans mixture | >240° C. |
| 32 | $CH_3$ | H, H | H, H | H, H | pyridine-2,5-diyl-bis(methylamine) | >240° C. |

-continued

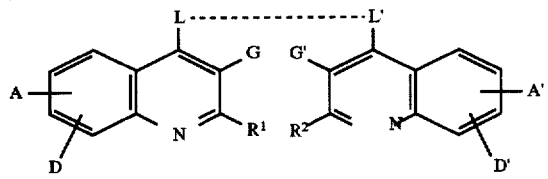

| Ex. No. | R¹/R² | A/A' | D/D' | G/G' | L/L' | M.p. (°C.)/ $R_f$ value* |
|---|---|---|---|---|---|---|
| 33 | $CH_3$ | H, H | H, H | H, H | ![structure] | 120° C. | a) Alox, solvent = methylene chloride/methanol/triethylamine 80:2:1
b) Alox, solvent = ethyl acetate/methanol 100:1

EXAMPLE 34
(2-Methyl-quinolin-2-yl)-[2-(2-methyl-quinolin-4-yloxy)-ethyl]amine

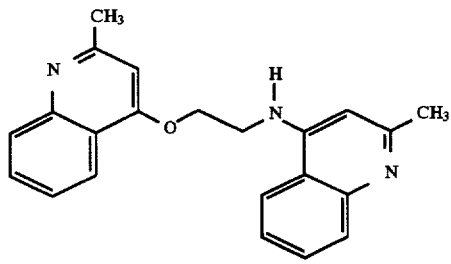

0.72 g (2.9 mmol) of 4-(2-hydroxyethyl)amino-2-methylquinoline hydrochloride, obtained from 4-chloroquinaldine and ethanolamine, in 20 ml of absolute DMF are treated with 100 mg (3.2 mmol) of 80% pure sodium hydride in paraffin under argon. After the mixture has been stirred for 1 hour at 50°, a further 0.3 g of 4-chloroquinaldine is added. After the mixture has been stirred for 20 hours at 50°, a further 100 mg of sodium hydride, as above, are added, and the mixture is stirred for a further 18 hours. The reaction batch is concentrated. Flash chromatography (silica gel K60; methylene chloride, then methylene chloride/ethanol/ammonia 100:10:1) gives a crude product which is purified by recrystallization from isopropanol. This gives 122 mg (22%) of colorless crystals, m.p. 247°–248° C.

EXAMPLE 35
(2-methyl- quinolin-4-yl)- [5- (2-methyl-quinolin- 4- yloxy) -pentyl]amine

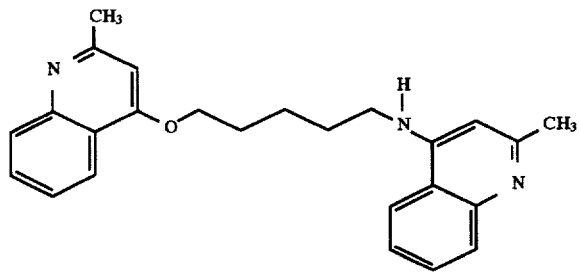

The title compound was prepared analogously to the protocol of Example 34 starting from 4-(5-hydroxypentyl) amino-2-methylquinoline.

m.p.: 222° C.

We claim:

1. A bisquinoline of the general formula (I)

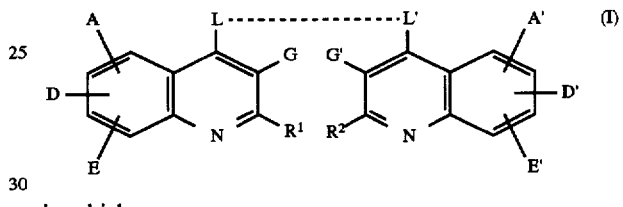

in which

E and E' denote hydrogen and $R^1$, $R^2$, A, A', D, D', G, and G', L and L' have the meanings given below

| R¹/R² | A/A' | D/D' | G/G' | L/L' |
|---|---|---|---|---|
| $CH_3$ | H, H | H, H | H, H | —N(H)—CH₂CH(Et)—N(H)— |
| H | 7-Cl, 7'-Cl | H, H | H, H | —N(H)—CH₂CH(Et)—N(H)— |
| $CH_3$ | H, H | H, H | H, H | —N(H)—(CH₂)₃—N(H)— |
| $CH_3$ | H, H | H, H | H, H | —N(Me)—CH₂CH₂—N(Me)— |
| $CH_3$ | H, H | H, H | H, H | —N(H)—CH₂CH₂—O—CH₂CH₂—N(H)— |
| $CH_3$ | H, H | H, H | H, H | —N(Me)—CH(CH(OH)Me)—(CH₂)₃—N(H)— x 2 HCl |
| $CH_3$ | H, H | H, H | H, H | —N(Me)—(CH₂)₆—N(Me)— |

-continued

| R¹/R² | A/A' | D/D' | G/G' | L/L' |
|---|---|---|---|---|
| CH₃ | H, H | H, H | H, H | (trans-cyclohexane-1,2-diyl-bis-NH-) |
| CH₃ | H, H | H, H | H, H | (cis-cyclohexane-1,2-diyl-bis-NH-) |
| CH₃ | H, H | H, H | H, H | (m-phenylene-bis-CH₂-NH-) |
| CH₃ | H, H | H, H | H, H | (pyridine-3,5-diyl-bis-CH₂-NH-) |
| CH₃ | H, H | H, H | H, H | (1,1-cyclohexane-bis-alkyl-NH-) |
| CH₃ | H, H | H, H | H, H | —HN—CH₂—CH₂—CHCH₃—CH₂CH₂—NH— |
| CH₃ | H, H | H, H | H, H | —HN—CH₂—CH₂—CHOH—CH₂CH₂—NH— |
| CH₃ | H, H | H, H | H, H | —HN—CH₂—CHOH—CH₂—NH— |
| CH₃ | H, H | H, H | H, H | —HN—CH₂—CH(OC₆H₅)—CH₂—NH— |
| CH₃ | H, H | H, H | H, H | —HN—CH₂—CH₂—S—CH₂—CH₂—NH— |
| CH₃ | H, H | H, H | H, H | —HN—CH₂—CH₂—SO—CH₂—CH₂—NH— |
| CH₃ | 5-CH₃, 5'-CH₃ | 7-CH₃, 7'-CH₃ | H, H | —NH—CH₂—CH₂—CH₂—CH₂—CH₂—NH— |
| CH₃ | 6-N(CH₃)₂, 6'-N(CH₃)₂ | H, H | H, H | —NH—CH₂—CH₂—CH₂—CH₂—CH₂—NH— |
| CH₃ | 6-CH(CH₃)₂, 6'-CH(CH₃)₂ | H, H | H, H | —NH—CH₂—CH₂—CH₂—CH₂—CH₂—NH— |
| CH₃ | 5-Cl, 5'-Cl | 8-CH₃, 8'-CH₃ | H, H | —NH—CH₂—CH₂—CH₂—CH₂—CH₂—NH— |
| CH₃ | 6-OCH₃, 6'-OCH₃ | H, H | H, H | —NH—CH₂—CH₂—CH₂—CH₂—CH₂—NH— |
| CH₃ | 8-F, 8'-F | H, H | H, H | —NH—CH₂—CH₂—CH₂—CH₂—CH₂—NH— |
| CH₃ | 7-N(CH₃)₂, 7'-N(CH₃)₂ | H, H | H, H | —NH—CH₂—CH₂—CH₂—CH₂—CH₂—NH— |
| CH₃ | 8-Cl, 8'Cl | H, H | H, H | —NH—CH₂—CH₂—CH₂—CH₂—CH₂—NH— |
| CH₃ | 6-OCH₃, 6'-OCH₃ | H, H | H, H | (trans-cyclohexane-1,4-diyl-bis-CH₂-NH-) |
| CH₃ | 6-OCH₃, 6'-OCH₃ | H, H | H, H | (cis-cyclohexane-1,4-diyl-bis-CH₂-NH-) |
| H | 7-CH₃, 7'-CH₃ | 8-CH₃, 8'-CH₃ | CH₃ | (cyclohexane-1,3-diyl-bis-CH₂-NH-, cis/trans mixture) |
| CH₃ | 8-CH₃, 8'-CH₃ | H, H | H, H | (cyclohexane-1,3-diyl-bis-CH₂-NH-, cis/trans mixture) |
| CH₃ | H, H | H, H | H, H | (pyridine-2,6-diyl-bis-CH₂-NH-) |
| CH₃ | H, H | H, H | H, H | (pyridine-2,4-diyl-bis-CH₂-NH-) |
| CH₃ | H, H | H, H | H, H | (pyridine-2,4-diyl-bis-CH₂-NH-) |
| CH₃ | H, H | H, H | H, H | —O—CH₂CH₂—NH— |
| CH₃ | H, H | H, H | H, H | —O—(CH₂)₄—NH— | or a salt thereof.

2. A method of treating a cerebral disorder in a patient in need of such treatment comprising administering to said patient an effective amount therefor of a bisquinoline of the formula (I)

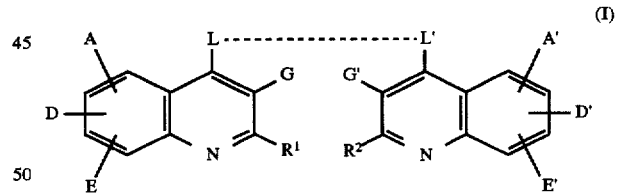

in which

A, A', D, D', E, E', G and G' are identical or different and represent hydrogen, halogen, cycloalkyl having 3 to 8 carbon atoms, aryl having 6 to 10 carbon atoms, cyano, carboxyl, hydroxyl, straight-chain or branched alkyl, alkoxy or alkoxycarbonyl, each of which has up to 8 carbon atoms, or represent a group of the formula —(CO)$_a$—NR³R⁴ in which a denotes a number 0 or 1,

R³ and R⁴ are identical or different and denote hydrogen or straight-chain or branched alkyl having up to 5 carbon atoms, L and L' together represent a radical of the formula

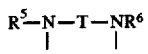

in which

R⁵ and R⁶ are identical or different and denote hydrogen, benzyl or straight-chain or branched alkyl having up to 4 carbon atoms and T denotes cycloalkyl having 3 to 6 carbon atoms or a straight-chain or branched alkyl chain having up to 10 carbon atoms which is optionally interrupted by an oxygen or sulfur atom, by a group of the formula —SO or —SO₂ or by phenyl, pyridyl or cycloalkyl having 3 to 8 carbon atoms and/or which is optionally substituted by phenoxy, spiro-linked cycloalkyl having 3 to 6 carbon atoms, hydroxyl or by straight-chain or branched alkoxy having up to 5 carbon atoms, or L and L' together represent a radical of the formula —O—(CH₂)$_b$—NR⁷— in which b denotes a number 2, 3, 4, 5, 6 or 7 and

R⁷ has the abovementioned meaning of R⁵ and R⁶ and is identical to or different from this meaning, and R and R² represent hydrogen or methyl, or a salt thereof.

3. The method according to claim 2, wherein the bisquinoline of the formula (I) employed is one in which A, A', D, D', E, E', G and G' are identical or different and represent hydrogen, fluorine, chlorine, bromine, cyclopropyl, cyclobutyl, cyclopentyl, cyclohexyl, phenyl, hydroxyl, straight-chain or branched alkyl, alkoxy or alkoxycarbonyl, each of which has up to 7 carbon atoms, or represent a group of the formula —(CO)$_a$—NR³R⁴ in which a denotes a number 0 or 1,

R³ and R⁴ are identical or different and denote hydrogen or straight-chain or branched alkyl having up to 4 carbon atoms, L and L' together denote a radical of the formula

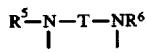

in which

R⁵ and R⁶ are identical or different and denote hydrogen, benzyl or straight-chain or branched alkyl having up to 3 carbon atoms and T denotes cyclopentyl, cyclohexyl or a straight-chain or branched alkyl chain having up to 8 carbon atoms which is optionally interrupted by an oxygen or sulfur atom, by a group of the formula —SO or —SO₂ or by phenyl, pyridyl, cyclopentyl, cyclohexyl or cycloheptyl and/or which is optionally substituted by phenoxy, spiro-linked cyclopentyl or cyclohexyl, hydroxyl or by straight-chain or branched alkoxy having up to 4 carbon atoms, or L and L' together represent a radical of the formula —O—(CH₂)$_b$—NR⁷— in which b denotes a number 2, 3, 4, 5 or 6 and

R⁷ has the abovementioned meaning of R⁵ and R⁶ and is identical to or different from this meaning, and R¹ and R² represent hydrogen or methyl, or a salt thereof.

4. The method according to claim 2, wherein the bisquinoline of the formula (I) employed is one in which A, A', D, D', E, E', G and G' are identical or different and represent hydrogen, cyclopropyl, cyclopentyl, cyclobutyl, cyclohexyl, phenyl, fluorine, chlorine, hydroxyl, straight-chain or branched alkyl or alkoxy, each of which has up to 3 carbon atoms, or represent a group of the formula —(CO)$_a$—NR³R⁴ in which a denotes a number 0 or 1, and

R³ and R⁴ are identical or different and denote hydrogen or straight-chain or branched alkyl having up to 3 carbon atoms, L and L' together represent a radical of the formula

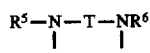

in which

R⁵ and R⁶ are identical or different and denote hydrogen, benzyl, methyl or ethyl and T denotes cyclohexyl or a straight-chain or branched alkyl chain having up to 7 carbon atoms which is optionally substituted by an oxygen or sulfur atom, by a group of the formula —SO or —SO₂ or by phenyl, pyridyl, cyclopentyl or cyclohexyl and/or which is optionally substituted by phenoxy, spiro- linked cyclohexyl, hydroxyl or by straight-chain or branched alkoxy having up to 3 carbon atoms, or L and L' together represent a radical of the formula —O—(CH₂)$_b$—NR⁷— in which b denotes a number 2, 3, 4 or 5 and

R⁷ has the abovementioned meaning of R⁵ and R⁶ and is identical to or different from this meaning, and R' and R² represent hydrogen or methyl, or a salt thereof.

5. Process for the preparation of a bisquinoline of the formula (I)

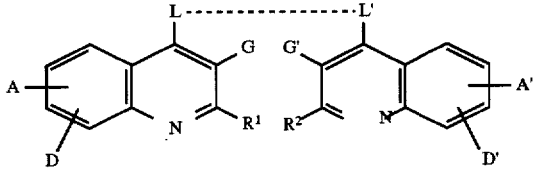
| $R^1/R^2$ | A/A' | D/D' | G/G' | L/L' |
|---|---|---|---|---|
| $CH_3$ | H, H | H, H | H, H | 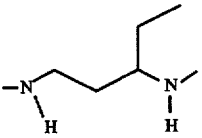 |
| H | 7-Cl, 7'-Cl | H, H | H, H | 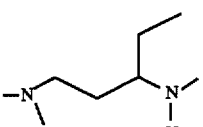 |
| $CH_3$ | H, H | H, H | H, H | 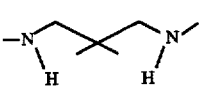 |
| $CH_3$ | H, H | H, H | H, H | 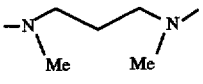 |
| $CH_3$ | H, H | H, H | H, H | 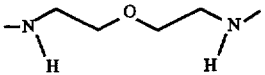 |
| $CH_3$ | H, H | H, H | H, H | 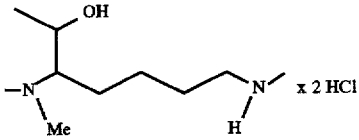 x 2 HCl |
| $CH_3$ | H, H | H, H | H, H | 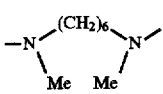 |
| $CH_3$ | H, H | H, H | H, H | 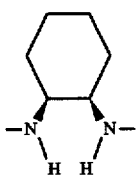 |
| $CH_3$ | H, H | H, H | H, H | 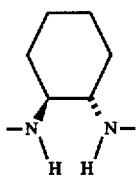 |
| $CH_3$ | H, H | H, H | H, H | 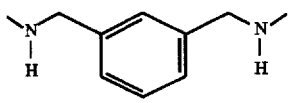 |
| $CH_3$ | H, H | H, H | H, H | 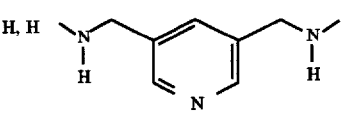 |

-continued

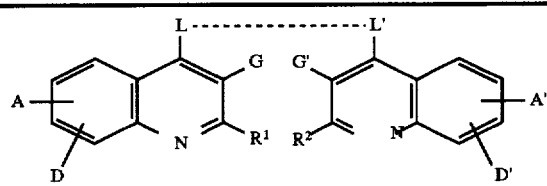

| R¹/R² | A/A' | D/D' | G/G' | L/L' |
|---|---|---|---|---|
| $CH_3$ | H, H | H, H | H, H | ![cyclohexane bis-aminomethyl/propyl linker] |
| $CH_3$ | H, H | H, H | H, H | $-HN-CH_2-CH_2-CHCH_3-CH_2-CH_2-NH-$ |
| $CH_3$ | H, H | H, H | H, H | $-HN-CH_2-CH_2-CHOH-CH_2CH_2-NH-$ |
| $CH_3$ | H, H | H, H | H, H | $-HN-CH_2-CHOH-CH_2-NH-$ |
| $CH_3$ | H, H | H, H | H, H | $-HN-CH_2-CH(OC_6H_5)-CH_2-NH-$ |
| $CH_3$ | H, H | H, H | H, H | $-HN-CH_2-CH_2-S-CH_2-CH_2-NH-$ |
| $CH_3$ | H, H | H, H | H, H | $-HN-CH_2-CH_2-SO-CH_2-CH_2-NH-$ |
| $CH_3$ | 5-$CH_3$, 5'-$CH_3$ | 7-$CH_3$, 7'-$CH_3$ | H, H | $-NH-CH_2-CH_2-CH_2-CH_2-CH_2-NH-$ |
| $CH_3$ | 6-$N(CH_3)_2$, 6'-$N(CH_3)_2$ | H, H | H, H | $-NH-CH_2-CH_2-CH_2-CH_2-CH_2-NH-$ |
| $CH_3$ | 6-$CH(CH_3)_2$, 6'-$CH(CH_3)_2$ | H, H | H, H | $-NH-CH_2-CH_2-CH_2-CH_2-NH-$ |
| $CH_3$ | 5-Cl, 5'-Cl | 8-$CH_3$, 8'-$CH_3$ | H, H | $-NH-CH_2-CH_2-CH_2-CH_2-CH_2-NH-$ |
| $CH_3$ | 6-$OCH_3$, 6'-$OCH_3$ | H, H | H, H | $-NH-CH_2-CH_2-CH_2-CH_2-CH_2-NH-$ |
| $CH_3$ | 8-F, 8'-F | H, H | H, H | $-NH-CH_2-CH_2-CH_2-CH_2-CH_2-NH-$ |
| $CH_3$ | 7-$N(CH_3)_2$, 7'-$N(CH_3)_2$ | H, H | H, H | $-NH-CH_2-CH_2-CH_2-CH_2-CH_2-NH-$ |
| $CH_3$ | 8-Cl, 8'-Cl | H, H | H, H | $-NH-CH_2-Ch_2-CH_2-CH_2-CH_2-NH-$ |
| $CH_3$ | 6-$OCH_3$, 6'-$OCH_3$ | H, H | H, H | [1,3-cyclohexane-bis-methylamine] trans |
| $CH_3$ | 6-$OCH_3$, 6'-$OCH_3$ | H, H | H, H | [1,3-cyclohexane-bis-methylamine] cis |
| H | 7-$CH_3$, 7'-$CH_3$ | 8-$CH_3$, 8'-$CH_3$ | $CH_3$ | [1,3-cyclohexane-bis-methylamine] cis/trans mixture |
| $CH_3$ | 8-$CH_3$, 8'-$CH_3$ | H, H | H, H | [1,3-cyclohexane-bis-methylamine] cis/trans mixture |
| $CH_3$ | H, H | H, H | H, H | [2,6-pyridine-bis-methylamine] |
| $CH_3$ | H, H | H, H | H, H | [2,4-pyridine-bis-methylamine] |
| $CH_3$ | H, H | H, H | H, H | [2,4-pyridine-bis-methylamine isomer] |
| $CH_3$ | H, H | H, H | H, H | [methoxyethyl-methylamine] |

-continued
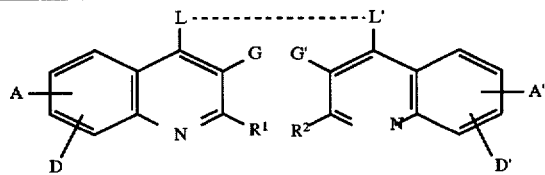
| R¹/R² | A/A' | D/D' | G/G' | L/L' |
|---|---|---|---|---|
| CH₃ | H, H | H, H | H, H |  |
in which
R¹, R², A, A', D, D', G, G', L and L' have the meanings
given below
| R¹/R² | A/A' | D/D' | G/G' | L/L' |
|---|---|---|---|---|
| CH₃ | H, H | H, H | H, H | 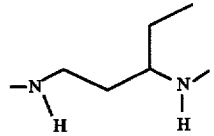 |
| H | 7-Cl, 7'-Cl | H, H | H, H | 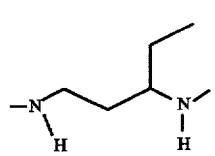 |
| CH₃ | H, H | H, H | H, H | 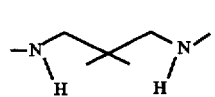 |
| CH₃ | H, H | H, H | H, H | 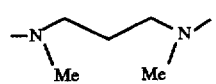 |
| CH₃ | H, H | H, H | H, H | 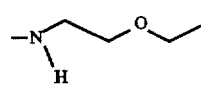 |
| CH₃ | H, H | H, H | H, H | 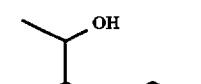 x 2 HCl |
| CH₃ | H, H | H, H | H, H | 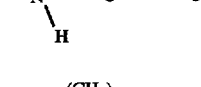 |
| CH₃ | H, H | H, H | H, H | 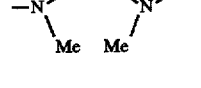 |

-continued

| R¹/R² | A/A' | D/D' | G/G' | L/L' |
|---|---|---|---|---|
| $CH_3$ | H, H | H, H | H, H | 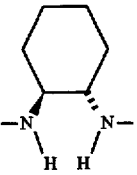 |
| $CH_3$ | H, H | H, H | H, H | 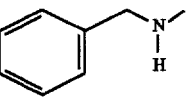 |
| $CH_3$ | H, H | H, H | H, H | 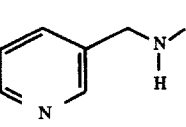 |
| $CH_3$ | H, H | H, H | H, H | 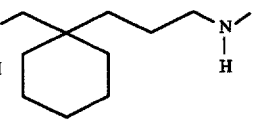 |
| $CH_3$ | H, H | H, H | H, H | $-HN-CH_2-CH_2-CHCH_3-CH_2CH_2-NH-$ |
| $CH_3$ | H, H | H, H | H, H | $-HN-CH_2-CH_2-CHOH-CH_2CH_2-NH-$ |
| $CH_3$ | H, H | H, H | H, H | $-HN-CH_2-CHOH-CH_2-NH-$ |
| $CH_3$ | H, H | H, H | H, H | $-HN-CH_2-CH(OC_6H_5)-CH_2-NH-$ |
| $CH_3$ | H, H | H, H | H, H | $-HN-CH_2-CH_2-S-CH_2-CH_2-NH-$ |
| $CH_3$ | H, H | H, H | H, H | $-HN-CH_2-CH_2-SO-CH_2-CH_2-NH-$ |
| $CH_3$ | 5-$CH_3$, 5'-$CH_3$ | 7-$CH_3$, 7'-$CH_3$ | H, H | $-NH-CH_2-CH_2-CH_2-CH_2-CH_2-NH-$ |
| $CH_3$ | 6-$N(CH_3)_2$, 6'-$N(CH_3)_2$ | H, H | H, H | $-NH-CH_2-CH_2-CH_2-CH_2-CH_2-NH-$ |
| $CH_3$ | 6-$CH(CH_3)_2$, 6'-$CH(CH_3)_2$ | H, H | H, H | $-NH-CH_2-CH_2-CH_2-CH_2-CH_2NH-$ |
| $CH_3$ | 5-Cl, 5'-Cl | 8-$CH_3$, 8'-$CH_3$ | H, H | $-NH-CH_2-CH_2-CH_2-CH_2-CH_2-NH-$ |
| $CH_3$ | 6-$OCH_3$, 6'-$OCH_3$ | H, H | H, H | $-NH-CH_2-CH_2-CH_2-CH_2-CH_2-NH-$ |
| $CH_3$ | 8-F, 8'-F | H, H | H, H | $-NH-CH_2-CH_2-CH_2-CH_2-CH_2-NH-$ |
| $CH_3$ | 7-$N(CH_3)_2$, 7'-$N(CH_3)_2$ | H, H | H, H | $-NH-CH_2-CH_2-CH_2-CH_2-CH_2-NH-$ |
| $CH_3$ | 8-Cl, 8'-Cl | H, H | H, H | $-NH-CH_2-CH_2-CH_2-CH_2-CH_2-NH-$ |
| $CH_3$ | 6-$OCH_3$, 6'-$OCH_3$ | H, H | H, H | 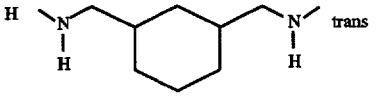 trans |
| $CH_3$ | 6-$OCH_3$, 6'-$OCH_3$ | H, H | H, H | 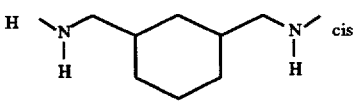 cis |
| H | 7-$CH_3$, 7'-$CH_3$ | 8-$CH_3$, 8'-$CH_3$ | $CH_3$ | 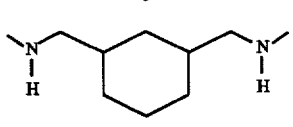<br>cis/trans mixture |
| $CH_3$ | 8-$CH_3$, 8'-$CH_3$ | H, H | H, H | 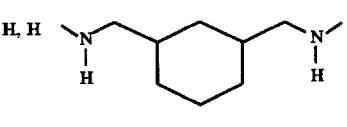<br>cis/trans mixture |
| $CH_3$ | H, H | H, H | H, H | 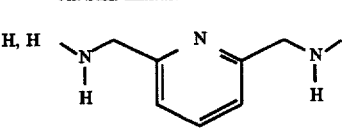<br>cis/trans mixture |

| R¹/R² | A/A' | D/D' | G/G' | L/L' |
|---|---|---|---|---|
| CH₃ | H, H | H, H | H, H | 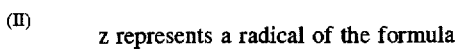 |
| CH₃ | H, H | H, H | H, H | 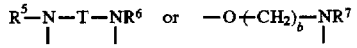 |
| CH₃ | H, H | H, H | H, H | 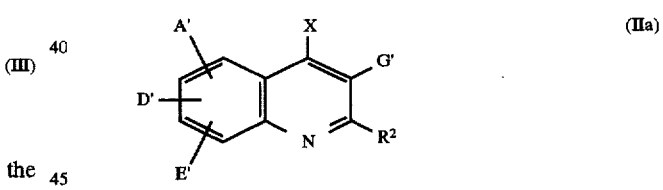 |
| CH₃ | H, H | H, H | H, H | 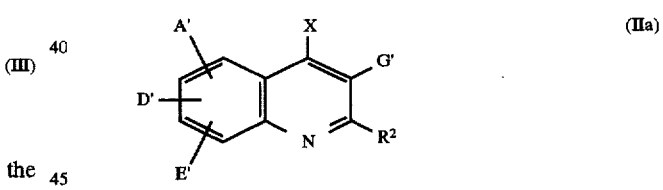 | which comprises

[A] reacting 2 equivalents of a compound of the formula (II)

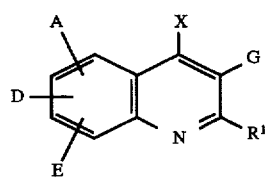

in which

A, D, E, G and R have the abovementioned meanings and x represents halogen, with a compound of the formula (III)

HL-L'H     (III)

in which

L and L' have the abovementioned meanings,
if appropriate in inert solvents and if appropriate in the presence of a base,
or

[B] reacting 1 equivalent of a compound of the formula (II) in an excess, with a compound of the formula (III) under the conditions of process [A] to give a compound of the formula (IV)

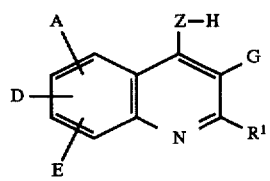

in which

A, D, E, G and R have the abovementioned meanings and z represents a radical of the formula $$R^5-N-T-NR^6 \quad \text{or} \quad -O + CH_2)_b - NR^7$$

in which $R^5$, $R^6$, $R^7$, b and T have the abovementioned meanings, and these are then reacted with a compound of the formula (IIa)

(IIa)

in which

A', D', E', G' and $R^2$ have the abovementioned meanings and x represents halogen, if appropriate in the presence of a base.

6. A pharmaceutical composition for treating a cerebral disorder comprising an effective amount therefor of a bis-quinoline according to claim 1 and a pharmaceutically acceptable carrier.

* * * * *

UNITED STATES PATENT AND TRADEMARK OFFICE
CERTIFICATE OF CORRECTION

PATENT NO. : 5,756,517
DATED : May 26, 1998
INVENTOR(S) : Schohe-Loop, et al.

It is certified that error appears in the above-identified patent and that said Letters Patent is hereby corrected as shown below:

Col. 23, Line 31      Before " and " delete " R " and substitute --- $R'$ ---

Col. 33, Line 34      After " and " delete " R " and substitute --- $R'$ ---

Col. 34, Line 24      After " and " delete " R " and substitute --- $R'$ ---

Signed and Sealed this

Fourteenth Day of December, 1999

Attest:

Q. TODD DICKINSON

Attesting Officer      Acting Commissioner of Patents and Trademarks